United States Patent [19]

Peloquin

[11] 4,281,235
[45] Jul. 28, 1981

[54] METHOD FOR WELDING FERROUS ALLOYS TO ALUMINUM AND ALUMINUM ALLOYS OR REFRACTORY METALS

[75] Inventor: Conrad Peloquin, San Leandro, Calif.

[73] Assignee: Tri Delta Industries, Inc., Hayward, Calif.

[21] Appl. No.: 82,983

[22] Filed: Oct. 9, 1979

[51] Int. Cl.³ .............................................. B23K 15/00
[52] U.S. Cl. ...................... 219/121 ED; 219/121 LD; 228/263 E
[58] Field of Search ................. 219/121 LC, 121 LD, 219/121 LE, 121 L, 121 LF, 121 LM, 121 EC, 121 EB, 121 ED, 121 EM, 121 EF, 121 EG, 121 EQ, 121 EL, 118; 228/263 E

[56] References Cited

U.S. PATENT DOCUMENTS

| 2,195,314 | 3/1940 | Lincoln ...................... 228/263 E X |
| 3,119,632 | 1/1964 | Skinner ...................... 228/263 E X |
| 3,121,948 | 2/1964 | Hollander et al. .......... 228/263 E X |
| 3,975,612 | 8/1976 | Nakazaki et al. ................ 219/118 X |

OTHER PUBLICATIONS

*Light Metal Age*, "Diffusion Bonding Aluminum to Stainless Steel", vol. 23, No. 910, p. 22, Oct., 1965.

*Primary Examiner*—C. L. Albritton
*Attorney, Agent, or Firm*—Manfred M. Warren; Robert B. Chickering; Glen R. Grunewald

[57] ABSTRACT

A method for welding ferrous alloys to aluminum alloys or refractory metals includes the step of coating the portion of the ferrous alloy to be welded with an intermediate metal compound or element such as gold alloy or silver. An accelerated particle beam is directed at the area to be welded, and is defocused so that approximately one third of the beam energy falls on higher melting point metal, while the remainder of the beam energy is directed to the portion of the lower melting point material adjacent to the weld line and subsequently melting it. The intermediate metal compound or element dissolves in the metal alloy having the lower melting point. As the melted alloy solidifies, the intermediate compound or element precipitates out of solution and diffuses to the interface of the alloy having the higher melting point. The diffused layer bonds to the higher melting point metal, to effect a metallurgical bond.

12 Claims, 9 Drawing Figures

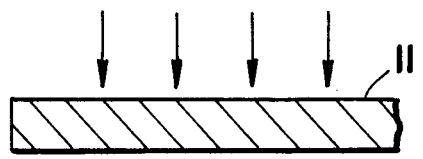
FIG_1
FIG_2
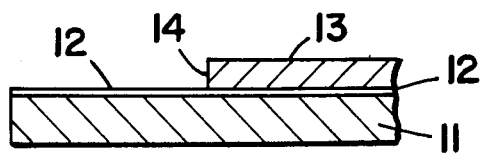
FIG_3
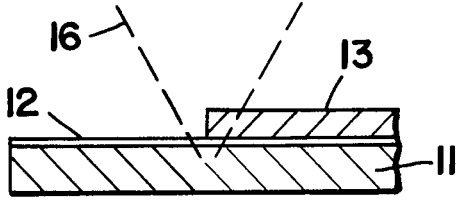
FIG_4
FIG_5
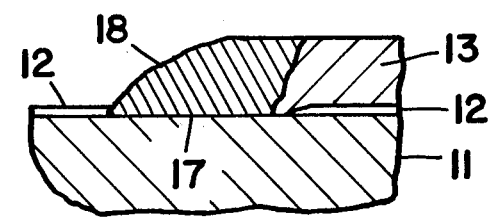
FIG_6
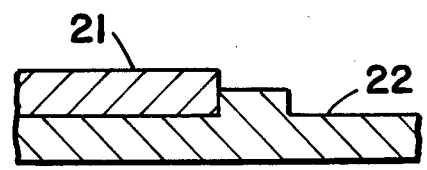
FIG_7
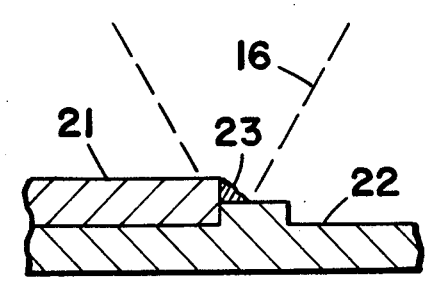
FIG_8
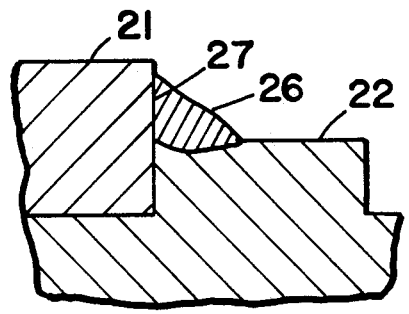
FIG_9

METHOD FOR WELDING FERROUS ALLOYS TO ALUMINUM AND ALUMINUM ALLOYS OR REFRACTORY METALS

BACKGROUND OF THE INVENTION

The joining of titanium and refractory materials such a tantalum to ferrous alloys, as well as the joining of aluminum alloys to ferrous alloys has presented significant problems in the prior art. These problems are a result of metallurgical incompatibilities, such as the limited solubilites of these materials in iron and ferrous alloys, the uncontrolled formation of intermetallic compounds, and also the rapid oxidation rates of some of the materials. These problems have prevented the development of a method for joining these materials which would be suitable for production and manufacturing purposes.

The following United States Patents comprise the prior art closest to the present invention: U.S. Pat. Nos. 3,935,417; 3,794,807; 3,463,901; 3,458,683; 3,999,030; 3,999,031; U.S. Pat. Nos. 3,808,395; 3,560,700; 3,294,951; 3,258,576; 4,063,062; 3,975,612.

The patents listed in the preceding paragraph are generally characterized as attempts in the prior art to employ electron beam or other particle acceleration welding techniques to join dissimilar metals which cannot be joined by conventional techniques. However, it is noted that none of these patents disclose the use of an accelerated particle beam to join aluminum alloys to ferrous alloys, nor to join refractory metal to ferrous alloys, as is shown by the present invention.

SUMMARY OF THE PRESENT INVENTION

The present invention generally comprises a method for joining metallurgically dissimilar metals which are difficult or impossible to join by conventional welding techniques. The method is particularly adapted for joining aluminum and aluminum alloys to ferrous alloys, and for joining refractory metals to ferrous alloys.

To join an aluminum or aluminum alloy to a ferrous alloy, the method provides for first depositing a thin layer of silver on the surface of the ferrous alloy. The silver may be deposited by ion sputtering, vapor deposition, or the like. In the case of a fillet weld, the aluminum alloy member is then placed in direct contact with the silver coated surface of the ferrous alloy member. In a vacuum or inert atmosphere, a high energy particle beam, (such as an electron beam) is directed toward the edge of the aluminum alloy member. The particle beam is defocused so that approximately one third of the beam intensity falls directly on the ferrous alloy member, while approximately two thirds of the beam intensity falls on the edge portion of the aluminum alloy member.

The high energy beam causes the faying edge of the aluminum alloy to melt, while the beam intensity is sufficient only to heat the ferrous alloy to a temperature which will allow a proportion of the silver substrate to melt directly adjacent thereto, the silver providing a wetting action on the surface of the ferrous alloy to permit the molten aluminum to wet the ferrous alloy surface.

The high energy beam is scanned along the edge of the aluminum alloy member, leaving behind the molten aluminum with the diffused silver interface, as the beam proceeds along the edge of the aluminum alloy material. As the molten aluminum solidifies, a portion of the dissolved silver precipitates from the solution onto the interface of the ferrous alloy. The precipitated silver forms a diffused interfacial layer which adheres tenaciously both to the ferrous alloy and to the resolidified aluminum alloy. Thus the two metal members are joined with a weld which is equal in strength or greater than the tensile strength of the aluminum alloy itself.

To join refractory metals to ferrous alloys, the method includes the steps of assembling the refractory metal member and the ferrous alloy member in the desired welded position, such as for a fillet weld or lap weld. A pure metal or alloy such as gold which has some mutual solubility (as determined by standard binary phase diagrams) is placed in the area of the fillet weld, and a high energy particle beam is directed toward the weld area. As before, the particle beam is defocused so that approximately one third of the beam energy falls on the higher melting point refractory material to effect heating to a temperature which will allow wetting. The remainder of the beam falls on the pure metal or alloy and on the ferrous alloy material adjacent to the weld line.

The high energy beam causes the pure metal or alloy as well as the ferrous alloy to melt directly adjacent to the weld line. The molten alloy then forms a solution at the weld line.

The high energy beam is directed to scan along the weld line, leaving behind the molten solution. As the molten solution solidifies, the pure metal precipitates from the solution and diffuses to the refractory metal interface. The pure metal or alloy diffused layer adheres tenaciously to the refractory metal, and also to the resolidified ferrous alloy. The weld thus formed is as strong as the lower tensile strength material without being brittle.

A BRIEF DESCRIPTION OF THE DRAWING

FIG. 1 is a schematic illustration of the first step of the method of the present invention.

FIG. 2 is a schematic depiction of the result of the first step of the method of the present invention.

FIG. 3 is a schematic depiction of the second step of the method of the present invention.

FIG. 4 is a schematic depiction of the third step of the method of the present invention.

FIG. 5 is a schematic depiction of the result of the step shown in FIG. 4.

FIG. 6 is an enlarged cross sectional elevation of the weld formed by the method of the present invention.

FIG. 7 is a schematic depiction of the first step of the method of the present invention, employed to join a refractory metal to a ferrous alloy.

FIG. 8 is a schematic depiction of the successive steps of the method shown in FIG. 7.

FIG. 9 is an enlarged cross sectional elevation of the weld formed by the method depicted in FIGS. 7 and 8.

DESCRIPTION OF THE PREFERRED EMBODIMENT

The present invention generally comprises a method for metallurgically joining dissimilar metals which are difficult or impossible to join by conventional welding or brazing techniques. Although the preferred embodiment description will describe two alternative embodiments of the method of the invention, it may be appreciated by those skilled in the art that the invention is not limited to the types of materials discussed nor the particular types of welds described.

The method of the present invention may be used to join an aluminum alloy member to a ferrous alloy member, as shown sequentially in FIGS. 1-5. As shown in FIG. 1, the ferrous alloy member 11, formed of stainless steel or the like, is coated with a thin layer of silver, as indicated by the arrows in FIG. 1. The silver coating 12, shown in FIG. 2, need be provided only in the immediate area to be welded. The silver layer 12 may be deposited by ion sputtering, vapor deposition, or the like.

An aluminum alloy member 13 is then disposed so that one surface thereof impinges on and is flush with the coating 12. For the purposes of illustration, it is assumed that the aluminum alloy member 13 is a sheet or bar having an edge 14 which extends perpendicularly to the plane of the figures. The weld to be formed is a fillet weld extending longitudinally in the vertex defined by the silver coating 12 and the edge 14 of the member 13.

The assembly shown in FIG. 3 is placed in a sealed chamber having a vacuum therein or a low pressure inert atmosphere. A high energy particle beam 16, such as an electron beam commonly used for welding, is then directed at the edge portion of the aluminum alloy member 13. The beam 16 is slightly defocused, so that the focal point of the beam is disposed below the surface of the member 11. Approximately two thirds of the beam energy is directed onto the edge portion of the member 13 directly adjacent to the edge 14. The remaining energy of the beam falls on the silver coating 12 directly adjacent to the edge 14, as shown in FIG. 4. It may be appreciated that the beam 16 is caused to translate or scan along the line of the weld to be formed; i.e., the beam travels along a line which extends orthogonally to the plane of the illustrating figures.

The intensity and energy of the beam 16 is insufficient to cause melting of the ferrous alloy of the member 11, although the beam does heat the local area of the member 11 adjacent to the edge 14. The beam intensity and energy is sufficient to melt the aluminum alloy of the member 13, the aluminum alloy having a melting point far lower than that of the member 11. With reference to FIG. 5, the aluminum alloy heated by the beam 16 is melted, and gravitally flows laterally from its initial position at the edge 14. The silver coating 12 provides a wetting action which permits the flow of molten aluminum along the surface of the ferrous alloy. At the same time, the molten aluminum dissolves a portion of the silver coating 12 that it contacts, thus creating a solution of silver in molten aluminum alloy.

As the particle beam 16 translates along the weld line, it leaves behind to cool the solution of aluminum alloy and silver. As the solution begins to cool, the silver precipitates from the solution and diffuses to the surface of the ferrous member 11. The diffused silver forms a thin layer directly on the surface of the ferrous member, and this silver member bonds to the ferrous alloy.

The result of the process described in the foregoing, as shown in FIG. 6, is a metallurgical union of the ferrous alloy member 11, the precipitated silver layer 17, and the melted and resolidified aluminum alloy 18. It may be appreciated that the resolidified aluminum alloy 18 bonds to the remaining unmelted aluminum alloy 13, so that the member 13 is joined by the portion 18 and 17 to the member 11. Tests have shown that a weld formed in the manner described in the preceding exhibits a tensile strength which is equal to or exceeds the tensile strength of the aluminum member 13.

Although the method shown in FIGS. 1-5 has been described with reference to a simple fillet weld, it may be appreciated by those having ordinary skill in the art that the technique described herein may be applied to many other forms of welding.

Another application of the method of the present invention is depicted in FIGS. 7-9, in which a ferrous alloy member 22 is joined by a fillet weld to a tantalum member 21. The first step in this alternative embodiment is the placing of an intermediate metal alloy in the vertex of the two members which are to be fillet welded. In this example, the intermediate alloy 23 is a gold alloy formed of approximately 82% gold and 18% nickel. As in the previous description, the weld line is disposed in the vertex defined by the member 21 and 22, the weld line extending perpendicularly to the plane of the drawings.

The high energy particle beam 16 is then caused to translate along the weld line. As before, approximately one third of the beam energy falls on the tantalum member 21 to provide a heating effect thereto, while the remaining beam energy falls on the gold alloy 23 and a small portion of the adjacent surface of the member 22. The beam energy is selected so that the member 21 is heated but not melted, while the gold alloy 23 and the adjacent portion of the member 22 are melted by the beam 16.

As the molten portion 26 cools, some of the gold from the alloy 23 begins to precipitate from the molten solucion and diffuse onto the surface of the member 21. The diffused layer 27 of gold thus deposited on the surface of the member 21 adheres to the tantalum metal. The molten metal 26 cools further and resolidifies, and forms a bond both with the gold layer 27 and with the ferrous metal of the member 22. The result is a continuous fillet weld joining the tantalum alloy member and the ferrous alloy member.

The method described with reference to FIGS. 7-9 can also be applied to join metals such as columbium, molybdenum, and other refractory metals to a broad range of ferrous alloy metals. Also, it may be appreciated that this method may be used to form other types of welds.

I claim:

1. A method for joining a first metal having a higher melting point to a second metal having a lower melting point, said first and second metals being substantially insoluble in one another, comprising depositing a thin layer of a third metal on the surface of one of said first and said second metals, placing the other of said first and said second metals in contact with said thin layer of third metal, directing a high energy particle beam over an area including the first metal, the second metal, and the third metal to heat the first metal, to partly melt the second metal, and to at least partly dissolve the third metal in the second metal, and cooling the resultant weld, said third metal melting at a temperature intermediate the melting temperature of said first metal and said second metal and being capable of wetting said first metal.

2. The method of claim 1 wherein said thin layer of third metal is deposited by ion sputtering.

3. The method of claim 1 wherein said thin layer of third metal is deposited by vapor deposition.

4. The method of claim 1, wherein said first metal comprises a ferrous alloy.

5. The method of claim 4, wherein said second metal comprises an aluminum alloy.

6. The method of claim 5, wherein said third metal substance comprises silver.

7. The method of claim 1, wherein approximately one-third of the energy of said beam is directed to the portion of said first member directly adjacent to said area.

8. The method of claim 7, wherein the remainder of said beam is directed to said third metal substance and to the portion of said second member directly adjacent to said area.

9. The method of claim 1, wherein said first metal comprises one of the refractory metals.

10. The method of claim 9, wherein said second metal comprises a ferrous alloy.

11. The method of claim 10, wherein said third metal substance comprises gold.

12. The method of claim 11, wherein said gold comprises approximately 82% gold and 18% nickel.

* * * * *